United States Patent [19]

Lee et al.

[11] Patent Number: 4,894,466
[45] Date of Patent: Jan. 16, 1990

[54] INTERMEDIATES AND PROCESSES FOR β-6-HYDROXYMETHYL HMG-COA REDUCTABLE INHIBITORS

[75] Inventors: Ta Jyh Lee; William F. Hoffman, both of Lansdale, Pa.

[73] Assignee: Merck & Co., Inc., Rahway, N.J.

[21] Appl. No.: 161,529

[22] Filed: Feb. 29, 1988

[51] Int. Cl.$^4$ ............................................ C07D 309/30
[52] U.S. Cl. ..................... 549/292; 549/214; 544/59; 544/60; 544/149; 544/359; 544/389; 546/207; 546/245; 548/518; 548/531
[58] Field of Search ................ 514/460; 549/292, 214

[56] References Cited

U.S. PATENT DOCUMENTS 4,444,784  4/1984  Hoffman et al. ..................... 549/292
4,582,915  4/1986  Sletienger et al. ................... 549/292

OTHER PUBLICATIONS

Hesse, *Adv. Free Rad. Chem.*, 3, 83–137 (1969).
D. H. R. Barton, *Pure Appl. Chem.*, 16, 1–15 (1968).
Akhtar, *Adv. Photochem*, 2, 263–304 (1964).

*Primary Examiner*—Richard L. Raymond
*Assistant Examiner*—Ba K. Trinh
*Attorney, Agent, or Firm*—Melvin Winokur; Joseph F. DiPrima

[57] ABSTRACT

This invention discloses intermediates and a process for the preparation of 6-desmethyl-6-β-hydroxymethyl derivatives of lovastatin and analogs thereof at the 8-acyl side chain.

4 Claims, No Drawings

INTERMEDIATES AND PROCESSES FOR β-6-HYDROXYMETHYL HMG-COA REDUCTABLE INHIBITORS

BACKGROUND OF THE INVENTION

Hypercholesterolemia is known to be one of the prime risk factors for ischemic cardiovascular disease, such as arteriosclerosis. Bile acid sequestrants have been used to treat this condition; they seem to be moderately effective but they must be consumed in large quantities, i.e. several grams at a time and they are not very palatable.

MEVACOR® (lovastatin), now commercially available, is one of a group of very active antihypercholesterolemic agents that function by limiting cholesterol biosynthesis by inhibiting the enzyme, HMG-CoA reductase. In addition to the natural fermentation products, mevastatin and lovastatin, there are a variety of semi-synthetic and totally synthetic analogs thereof.

The naturally occurring compounds and their semi-synthetic analogs have the following general structural formulae:

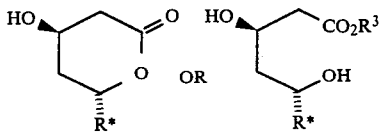

wherein:
$R^3$ is hydrogen, $C_{1-5}$ alkyl or $C_{1-5}$ alkyl substituted with a member of the group consisting of phenyl, dimethylamino, or acetylamino; and
$R^*$ is

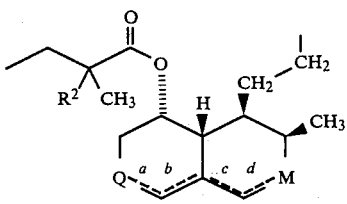

wherein
Q is

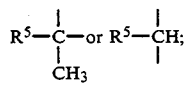

$R^5$ is H or OH; M is

$R^6$ is hydrogen or hydroxy;
$R^2$ is hydrogen or methyl; and a, b, c, and d represent single bonds, one of a, b, c or d represents a double bond, or both a and c or both b and d represent double bonds provided that when a is a double bond, Q is

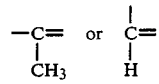

and when d is a double bond, M is

U.S. Pat. No. 4,517,373 discloses semisynthetic hydroxy containing compounds represented by the above general formula wherein $R^*$ is

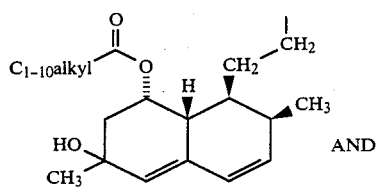

AND

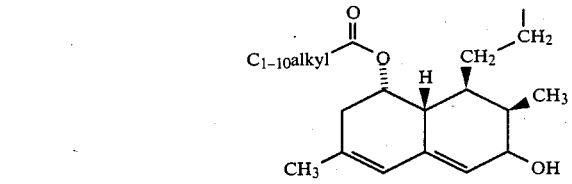

U.S. Pat. No. 4,537,859 and U.S. Pat. No. 4,448,979 also disclose semi-synthetic hydroxy-containing compounds represented by the above general formula wherein $R^*$ is

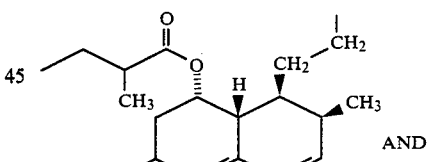

AND

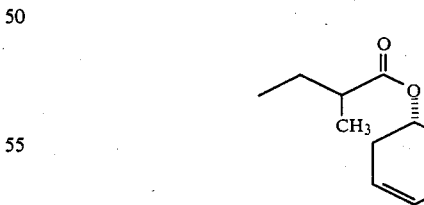

These compounds are prepared by the action of certain microorganisms on the corresponding non-hydroxylated substrates. One such organism described in U.S. Pat. No. 4,537,859 is of the genus Nocardia.

U.S. Pat. No. 4,376,863 discloses a fermentation product, isolated after cultivation of a microorganism belonging to the genus Aspergillus, which has a hydroxy containing butyryloxy side chain and is represented by the above general formula wherein $R^*$ is

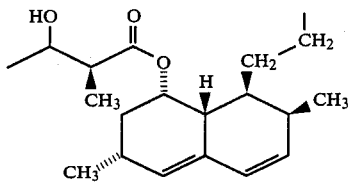

Japanese unexamined patent application J59-122,483-A discloses a semi-synthetic hydroxy-containing compound represented by the above general formula wherein R* is

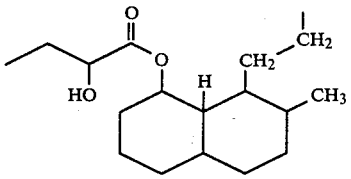

Copending U.S. patent application Ser. No. 048,136 filed May 15, 1987 discloses 6-substituted compounds of the above general formula wherein R* is

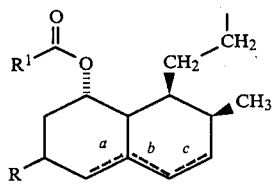

wherein R is $CH_2OH$,

$CH_2OCR^4$, $CO_2R^7$ or $CNR^8R^9$;

and $R^1$, $R^4$, $R^7$, $R^8$ and $R^9$ are broadly defined organic moieties.

The compounds of the above-mentioned U.S. patent application, Ser. No. 048,136 wherein a and c are double bonds were prepared by a microbiological conversion of lovastatin or an analog thereof with a 6-methyl substituent. Compounds where one of a, b or c represent a double bond or a, b, c all represent single bonds were prepared by a synthetic sequence from the 8-hydroxy-6-methyl derivative.

Copending U.S. patent application Ser. No. 131695 filed Dec. 11 1987 discloses a intermediates and processes for preparing 6-desmethyl-6-carboxy derivatives of lovastatin and 8-acyl analogs wherein the 6-carboxy moiety has the alpha stereochemical configuration.

Copending U.S. patent applications, Ser. No. 161530 and 16/579 filed 2-29-88, disclose intermediates and processes for preparing 6-desmethyl-6-hydroxymethyl derivatives of lovastatin and 8-acyl analogs, wherein the 6-hydroxymethyl moiety has the alpha stereochemical configuration.

The literature discloses a reaction known as the Barton Reaction by which a hydrogen on the γ carbon to a COH group can be abstracted to afford a carbon radical which can be oxidized. (See Hesse Adv. Free-Radical Chem. 3, 83–137 (1969); Barton, Pure Appl. Chem. 16, 1–15 (1968); Arthar, Adv. Photochem. 2, 263–304 (1964).

DETAILED DESCRIPTION OF THE INVENTION

This invention relates to novel intermediates, and a novel process for their preparation, where said intermediates are useful in a novel preparation of 6-desmethyl-6-β-hydroxymethyl (I) derivatives of lovastatin and 8-acyl analogs thereof wherein the 6-hydroxymethyl moiety has the beta stereochemical configuration. Said 6-hydroxymethyl derivatives of lovastatin and analogs thereof are useful in treating hypercholesterolemia and are disclosed in copending patent application, Ser. No. 48,136 filed May 15, 1987.

The overall process of this invention for preparing the 6-desmethyl-6-β-hydroxymethyl (I) derivatives of lovastatin is shown in scheme 1.

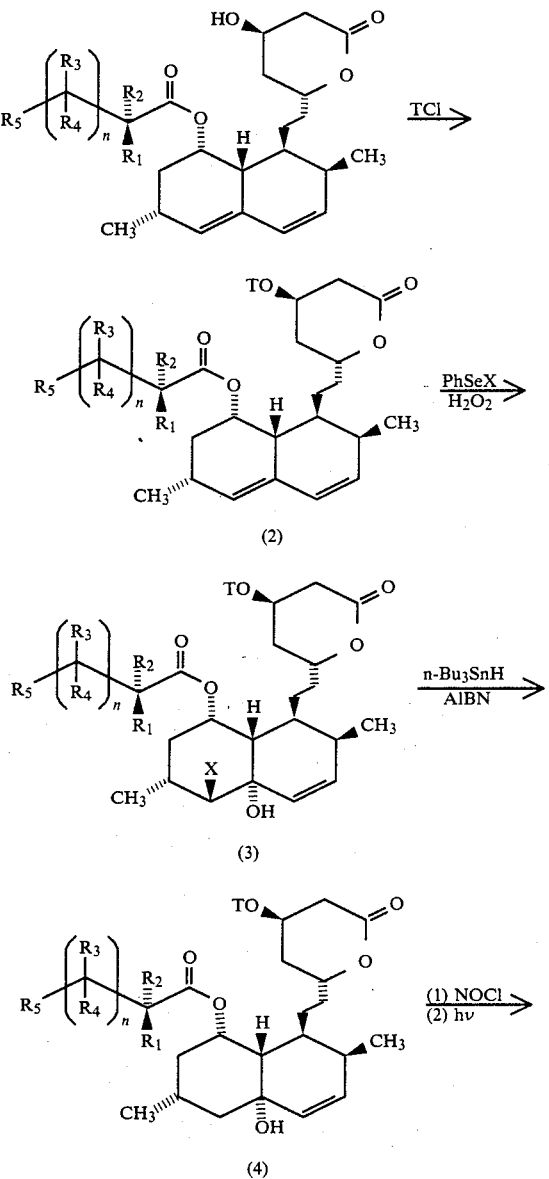

-continued
SCHEME 1

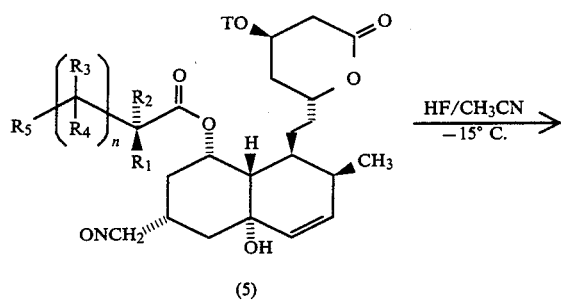
(5)

HF/CH₃CN
−15° C.

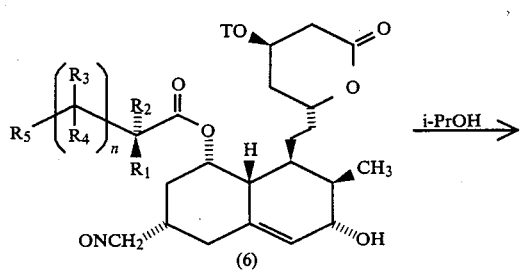
(6)

i-PrOH

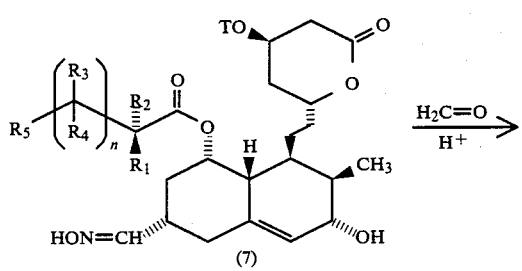
(7)

H₂C=O
H⁺

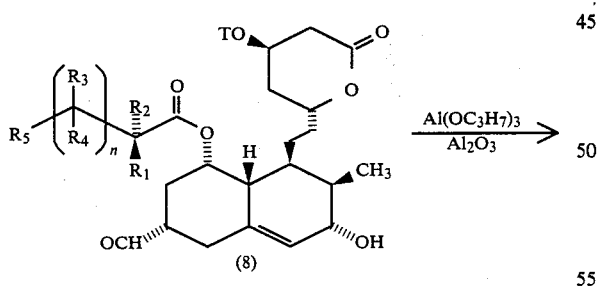
(8)

Al(OC₃H₇)₃
Al₂O₃

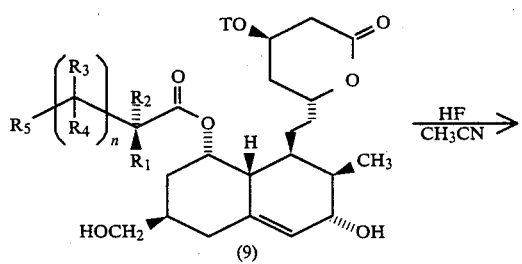
(9)

HF
CH₃CN

-continued
SCHEME 1

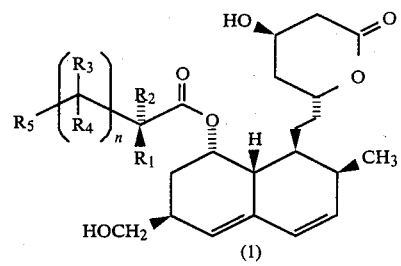
(1)

The intermediates (8) of the present invention are prepared in a novel process (i) which comprises:
(A) treating the starting material (1)

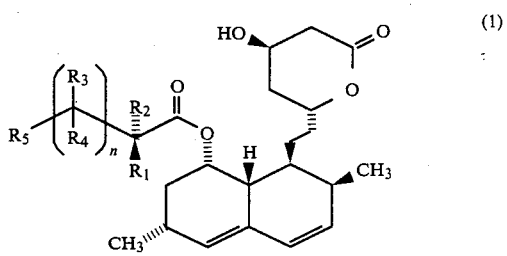
(1)

wherein:
n is 0 to 3;
$R_1$ and $R_2$ independently are hydrogen, $C_{1-5}$ alkyl, or $R_1$ and $R_2$ together with the carbon atom to which they are attached form a carbocyclic ring of 3 to 8 carbon atoms;
$R_3$ and $R_4$ are independently hydrogen, $C_{1-3}$ alkyl, $C_{3-7}$ cycloalkyl, $C_{1-3}$ alkylthio, phenyl, phenylthio or substituted phenyl in which the substituents are V and W and when n is 2 to 3, each of the $R_3$s and $R_4$s are independently hydrogen, $C_{1-3}$ alkyl, $C_{3-7}$ cycloalkyl or only one of the $R_3$s or $R_4$s on the chain of carbons is phenyl or substituted phenyl;
$R_5$ is hydrogen, tosylate, OT, $C_{1-5}$ alkyl or $C_{1-5}$alkyl substituted with tosylate or OT, $C_{3-7}$ cycloalkyl or $C_{3-7}$ cycloalkyl substituted with $C_{1-3}$ alkyl, tosylate or OT; $C_{2-5}$ alkenyl, phenyl or substituted phenyl in which the substituents are V and W, or $R_5$ is a group selected from:
(a) $C_{1-5}$-alkanoyloxy-$C_{1-4}$-alkyl,
(b)

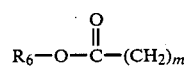

in which m is 0 to 3 and $R_6$ is $C_{1-5}$ alkyl;
(c)

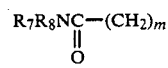

in which $R_7$ and $R_8$ are independently $C_{1-5}$ alkyl or $R_7$ and $R_8$ together with the nitrogen atom to which they are attached form a heterocycle selected from piperidinyl, morpholinyl, pyrrolidinyl, piperzinyl or thiomorpholinyl;
(d)

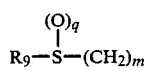

in which q is 0 to 2 and R9 is C1-5 alkyl or phenyl or substituted phenyl in which the substituents are V and W;

V and W independently are hydrogen, halogen, hydroxy, trifluoromethyl, C1-3 alkyl, C1-3 alkyloxy and TO-C1-3 alkyl; with a hydroxyl protecting compound such as tert-butyldimethylsilyl chloride, tert-butyldiphenylsilyl chloride, trimethylsilyl chloride, triethylsilyl chloride, triisopropylsilyl chloride or dihydropyran to yield a compound (2) wherein

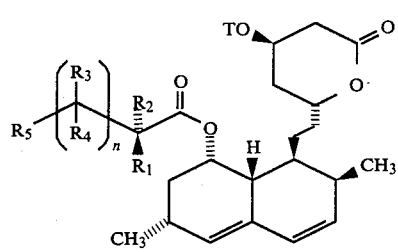
(2)

T is a hydroxyl protecting group such as tert-butyldimethylsilyl, tert-butyldiphenylsilyl, trimethylsilyl, triethylsilyl, triisopropylsilyl or tetrahydropyranyl;

(b) contacting the compound (2) with a halogenating agent such as a phenylselenyl halide or phenylsulfinyl chloride in an inert solvent at about −80° C. then treating the product with an oxidizing agent such as hydrogen peroxide or a peroxyacid in an ethereal solvent at ambient temperature to yield a compound (3) wherein X=Cl or Br;

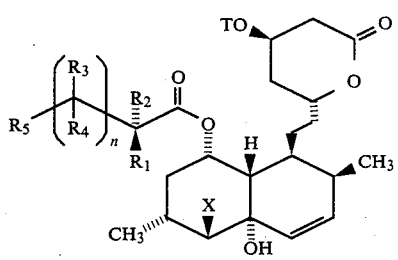
(3)

(c) treating the compound (3) with a trialkyl or triaryltin hydride such as tri(n-butyl)tin hydride and a radical initiator such as azobisisobutyronitrile to yield a compound (4);

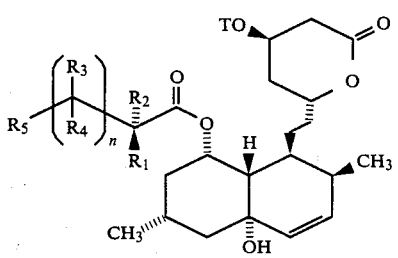
(4)

(d) contacting the compound (4) with nitrosyl chloride and base, followed by irradiation with light to yield a compound (5);

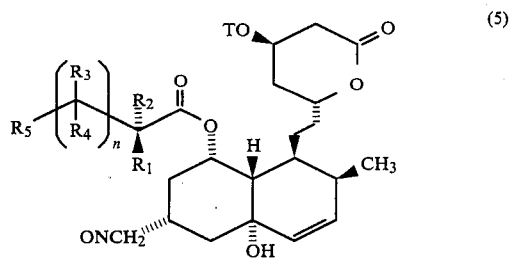
(5)

(e) treating compound (5) with an acidic mixture in a polar solvent such as HF/CH3CN at about −15° C. to afford compound (6)

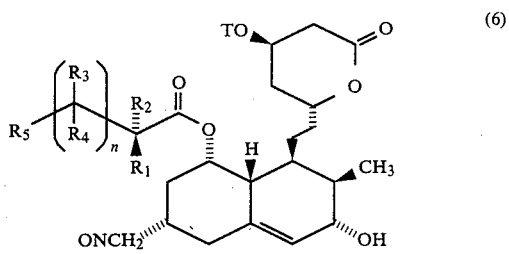
(6)

(f) heating the compound (6) in a protic solvent such as isopropanol to afford compound (7)

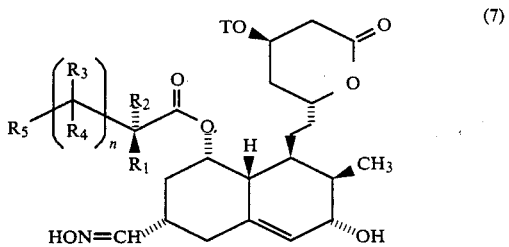
(7)

(g) treating compound (7) with an aqueous paraformaldehyde solution in the presence of an acid catalyst to yield compound (8):

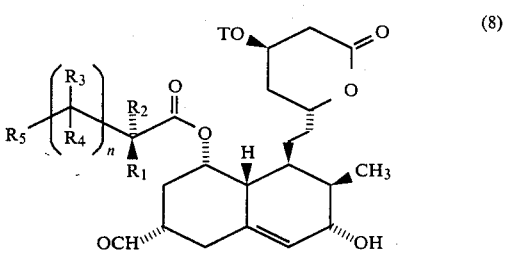
(8)

Intermediates (8) are used to form intermediates (9) in a novel process (ii) which comprises:

(h) contacting compound (8) with aluminum isopropoxide and aluminum oxide in an alcoholic solvent to yield compound (9):

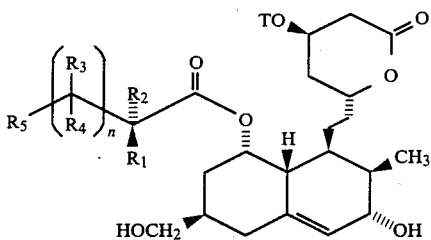

Products (I) are formed from intermediates (9) in a novel process (iii) which comprises:
(i) contacting intermediate (9) with an acid in a polar solvent to yield compound (I):

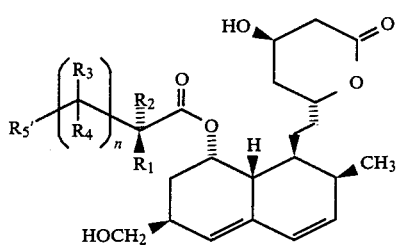

wherein $R_5'$ is identical to $R_5$ except that any OT protecting group is hydrolyzed to OH.

It should be understood that the alkyl, alkylthio, alkenyl and alkanoyl groups of this invention may either be in a straight chain or branched configuration.

One embodiment of this invention is the compounds of formula (8):

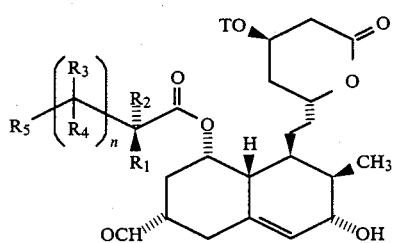

wherein n, $R_1$, $R_2$, $R_3$, $R_4$, $R_5$ and T are defined above. In one class of this embodiment are the compounds of formula (3) wherein:
$R_1$ is methyl;
$R_2$ is hydrogen or methyl;
$R_3$ and $R_4$ are independently hydrogen or $C_{1-3}$alkyl.
In a subclass:
$R_5$ is hydrogen, tosylate, OT, $C_{1-5}$alkyl, phenyl or substituted phenyl in which the substituents are V and W;
T is tert-butyldimethylsilyl.
Exemplifying this subclass are compouns (8) wherein:
(1) n is 0, $R_2$ is methyl, $R_5$ is ethyl;
(2) n is 0, $R_2$ is hydrogen, $R_5$ is ethyl.

A second embodiment of this invention is the process for the preparation of intermediates (8) from starting material (1). This process consists of (a) contacting compound (1) with a hydroxyl protecting compound; (b) treatment with a halogenating agent in an inert solvent followed by treatment with an oxidizing agent in an ethereal solvent; (c) treatment with a trialkyl or triaryltin hydride and a radical initiator; (d) contact with nitrosyl chloride followed by irradiation with light; (e) treatment with HF/CH$_3$CN; (f) contact with isopropanol; (g) treatment with paraformaldehyde.

A third embodiment of the instant invention is the compounds of formula (9):

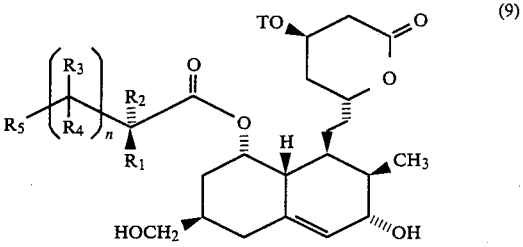

wherein n, $R_1$, $R_2$, $R_3$, $R_4$, $R_5$ and T have the same values as in the general embodiment of compounds (8). In one class of this embodiment are the compounds of formula (9) wherein:
$R_1$ is methyl;
$R_2$ is hydrogen or methyl;
$R_3$ and $R_4$ are independently hydrogen or $C_{1-3}$ alkyl.
In a subclass:
$R_5$ is hydrogen, tosylate, OT, $C_{1-5}$alkyl, phenyl or substituted phenyl in which the substituents are V and W;
T is tert-butyldimethylsilyl.
Exemplifying this subclass are compounds (9) wherein:
(1) n is 0, $R_2$ is methyl, $R_5$ is ethyl;
(2) n is 0, $R_2$ is hydrogen, $R_5$ is ethyl.

A fourth embodiment of the present invention is the process for the preparation of intermediates (9) from intermediates (8). This process consists in contacting a compound of formula (8) with aluminum isopropoxide and aluminum oxide.

Starting material (1) is treated with a reagent suitable for protecting the alcohol group at the lactone 4-position. Examples of suitable reagents are trialkylsilyl chlorides, dialkylarylsilyl chlorides and dihydropyran.

The diene (2) of step (B) is treated with a halogenating agent such as phenylselenyl chloride or bromide or phenylsulfinyl chloride, preferably phenylselenyl chloride, in an approximately equimolar ratio in an inert solvent at about −80° C., for approximately 20 minutes; illustrative of such inert solvents are methylene chloride, ether and the like. After a standard workup the product residue is dissolved in an ethereal solvent, chilled to about 0° C. and oxidized with an agent such as 30% hydrogen peroxide or a peroxy acid such as peroxybenzoic acid to yield a halohydrin analog (3).

Intermediate (3) is treated with a halide reducing agent such as a trialkyltin hydride or a triaryltin hydride, preferably tri-n-butyltin hydride and a radical initiator such as azobisisobutyronitrile (AIBN) in an inert solvent such as benzene at a temperature between 70° C. and 100° C. preferably about 90° C. for 0.5 to 5 hours preferably 2 hours.

Compound (4) is treated with nitrosyl chloride at a temperature between −10° and 10° C., preferably 0° C. for several minutes in a basic solvent until TLC analysis of an aliquot showed the reaction to be complete. Illustrative of such basic solvents are pyridine and quinoline and the like. In a second step the irradiaton is conducted using light of wavelength greater than 320 Å. Once source of the irradiation is a medium pressure mercury lamp, at a temperature between 0° and 30° C., preferably at about 20° C., for a period of from 0.5 to 5 hours, most preferably about 0.7 hours at 20° C., in an inert solvent such as benzene, pyridine, hexane or the like, or a mixture of inert solvents.

Compound (5) is treated with an aqueous acidic mixture such as approximately 48% HF or perchloric acid in a polar solvent such as acetonitrile or aqueous acetone at a temperature between −20° C. and 10° C., preferably 48% HF/CH$_3$CN at about −15° C.

The rearrangement of a compound of formula (6) to a compound of formula (7) is conducted at a temperature between 60° and 100° C., preferably at about 95° C. for a period of 0.5 to 10 hours, most preferably for 2 hours at about 95° C., in a protic solvent and an amine base. Illustrative of such protic solvents are alcohols such as isopropanol or 2-butanol and the like. Examples of amine bases are pyridine, triethylamine, quinoline, and the like.

The conversion of an oxime (7) to an aldehyde (8) is conducted using an approximately 40% aqueous paraformaldehyde solution and a carboxylic acid such as acetic acid.

The aldehyde (8) is converted into a hydroxymethyl alcohol of beta stereochemical configuration by treatment with aluminum isopropoxide and aluminum oxide in an alcohol at a temperature between 80° to 100° C. for 80 hours, preferably about 90°–95° C. for approximately 60 hours. Approximately one third of the total amountof aluminum isoproxide and aluminum oxide is added initially and the remainder after about 22 hours. The total mole ratio of aluminum isopropoxide to aldehyde (8) is 1.5:1. Examples of appropriate alcohols are isopropanol and 2-butanol.

Intermediate (9) is dehydrated and the silyl ether or tetrahydropyranyl group removed by treatment with an aqueous acid in a polar solvent, preferably hydrofluoric acid in acetonitrile, most preferably 48% hydrofluoric acid in acetonitrile, at 0° to 60° C., preferably 55°–60° C. for about 1 hour.

Starting compounds (1) wherein the acyl side chain is other than 2-methylbutyryloxy are prepared from lovastatin by hydrolysis of the 8-acyl side chain, following the procedure in U.S. Pat. No. 4,444,784, followed by acylation with an appropriate alkanoyl chloride in the presence of lithium bromide and dimethylaminopyridine in pyridine using the procedure in copending U.S. Application Ser. No. 038,580 filed Apr. 15, 1987. Alternatively, the acylation is conducted with an alkanoyl chloride or an alkanoic acid under standard reaction conditions. The alkanoyl chloride can be formed by standard chemical transformations such as substitution with an alkyl moiety or other appropriate electrophile at an acidic C-H site on an available starting material.

The following examples illustrate the present invention and as such are not to be considered as limiting the invention set forth in the claims appended hereto.

EXAMPLE 1

Preparation of 6(R)-[2-[6(S)-hydroxymethyl-8(S)-(2,2-Dimethylbutyryloxy)-2(S)-methyl-1,2,6,7,8,8a(R)-hexahydronaphthyl-1(S)]ethyl]-4(R)-hydroxy-3,4,5,6-tetrahydro-2H-pyran-2-one (a)
6(R)-[2-[8(S)-(2,2-Dimethylbutyryloxy)-2(S),6(R)-dimethyl-1,2,6,7,8,8a(R)-hexahydronaphthyl-1(S)]-ethyl]-4(R)-(t-butyldimethylsilyloxy)-3,4,5,6-tetrahydro-2H-pyran-2-one (2α)

Tert-Butyldimethylsilyl chloride (8 g, 52 mmol) was added to a stirred solution of 6(R)-[2-[8(S)-(2,2-Dimethylbutyryloxy)-2(S),6(R)-dimethyl-1,2,6,7,8,8a(R)-hexahydronaphthyl-1(S)]ethyl]-4(R)-hydroxy-3,4,5,6-tetrahydro-2H-pyran-2-one (20 g, 48 mmol) and imidazole (6.8 g, 0.1 mol) in DMF (150 mL) at 0° C. The resulting mixture was stirred at 0° C. for 5 minutes, then warmed to room temperature and stirred for 5 hours. TLC analysis of an aliquot indicated that the reaction was complete. The reaction mixture was poured into cold water and extracted with ether. The ethereal extract was washed with dilute hydrochloric acid, water and 5% sodium bicarbonate solution. After drying over MgSO$_4$, the organic extract was filtered and the filtrate was concentrated in vacuo to afford the desired product as a colorless, viscous oil: NMR (CDCl$_3$) δ 0.84 (3H, t, J=7 Hz), 0.89 (3H, J=7 Hz), 0.90 (9H, s), 1.09 (3H, d, J=7 Hz), 1.11 (3H, s), 1.12 (3H, s), 4.30 (H, m), 4.60 (H, m), 5.33 (H, m), 5.51 (H, m), 5.77 (H, d of d, J=10, 6 Hz), 5.98 (H, d, J=10 Hz).

(b)
6(R)-[2-[5(S)-Chloro-4a-(S)-hydroxy-8(S)-(2,2-dimethylbutyryloxy)-2(S),6(R)-dimethyl-1,2,4a,5,6,7,8-,8a(S)-octahydronaphthyl-1(S)]ethyl]-4(R)-(t-butyldimethylsilyloxy)-3,4,5,6-tetrahydro-2H-pyran-2-one (3′)

A solution of phenylselenyl chloride (10 g, 52 mmol) in methylene chloride (50 ml) was added dropwise to a stirred solution of compound 2′ (25.2 g, 48 mmol) in methylene chloride (350 mL) cooled in a dry ice/i-propanol bath (−78° C.). The resulting mixture was stirred at −78° C. for 20 minutes, poured into cold water (300 mL) and extracted with ether twice (400 mL, then 150 mL). The combined extracts were dried (MgSO$_4$), filtered and concentrated to afford an oily residue which was dissolved in tetrahydrofuran (300 mL). This solution was chilled in an ice bath (0° C.), and 30% hydrogen peroxide (15 mL) was added. The resulting mixture was stirred at 0° C. for 5 minutes, then warmed to room temperature and stirring continued for 1 hour. The reaction mixture was poured into cold water and extracted with chloroform three times (400 mL, then 2×100 mL). The combined extracts were dried (MgSO$_4$), filtered and concentrated to yield a residue which was purified by flash chromatography on a silica gel column. Elution was hexane:ethyl acetate (5:1/v:v) removed the impurities. Further elution with hexane:ethyl acetate (4:1/v:v) provided the title compound as a pale yellow gum which later solidified on standing: mp 117°–8° C., NMR (CDCl$_3$) δ 0.075 (3H, s), 0.08 (3H, s), 0.85 (3H, t, J=7 Hz), 0.88 (9H, s), 0.89 (3H, d, J=7 Hz), 1.15 (3H, s), 1.16 (3H, s), 1.32 (3H, d, J=7 Hz), 1.58 (2H, q, J=7 Hz), 3.39 (H, s), 4.05 (H, bs), 4.30

(H, m), 4.60 (H, m), 5.32 (H, m), 5.59 (H, d, J=11 Hz), 5.79 (H, d of d, J=11, 6 Hz).

Anal. calcd. for C₃₁H₅₃Cl₀₆Si: C, 63.61; H, 9.13. Found: C, 63.80; H, 9.04.

(c)
6(R)-[2-[4a(S)-hydroxy-8(S)-(2,2-dimethylbutyryloxy)-2(S),6(R)-dimethyl-1,2,4a,5,6,7,8,8a(S)-octahydronaphthyl-1(S)]ethyl]-4(R)-(t-butyldimethylsilyloxy)-3,4,5,6-tetrahydro-2H-pyran-2-one (4')

Tributyltin hydride (7.06 ml, 26.25 mmol) and azobisisobutyronitrile (AIBN) (0.82 g 5.0 mmol) were added to a magnetically stirred solution of chlorohydrin 3' (8.78 g, 15 mmol) in benzene (100 ml). The resulting solution was refluxed for 2 hours, cooled and concentrated in vacuo to a viscous yellow oil which was stirred with pet ether (200 ml) at −15° C. (ice/acetone bath) to provide 4' as a fluffy, colorless solid (6.9 g, mp 97°–9° C.). The filtrate was extracted with CH₃CN (4×50 ml) to remove all of the product contained in the pet ether. The CH₃CN extracts were combined and concentrated to a colorless oil which was purified by flash chromatography on a silica gel column. Elution with ethyl acetone/hexane (1:3/v:v) gave a colorless solid (1.0 g) which was stirred in pet ether (25 ml) at 0° C. to remove some tin residues. The mixture was filtered to provide the product 4' as a colorless solid. M.P. 103°–4° C., nmr (CDCl₃) δ 0.07 (3H, s), 0.08 (3H, s), 0.88 (9H, s), 1.15 (3H, s), 1.16 (3H, s), 1.20 (3H, d, J=7 Hz), 2.78 (H, s), 4.28 (H, m), 4.58 (H, m), 5.30 (H, m), 5.58 (H, d J=10 Hz), 5.67 (H, dd, J=10, 5 Hz).

Anal. Calcd. for C₃₁H₅₄O₆Si: C, 67.59; H, 9.88. Found: C, 67.20; H, 9.99.

(d)
6(R)-[2-[4a(S)-hydroxy-8(S)-(2,2-dimethylbutyryloxy)-2(S)-methyl-6(R)-nitrosylmethyl-1,2,4a,5,6,7,8,8s(S)-octahydronaphthyl-1(S)]ethyl]-4(R)-(t-butyldimethylsilyloxy)-3,4,5,6-tetrahydro-2H-pyran-2-one (5')

Nitrosyl chloride gas was bubbled through a stirred solution of compound 4' (1.25 g, 2.27 mmol) in pyridine (25 ml) at 0° C. for several minutes until the reaction mixture became a dark brown color. An aliquot was taken and partitioned between ether and water. If TLC analysis¹ of the ether layer indicated the completion of the reaction, the reaction mixture was poured into an ice/water mixture (50 ml) and extracted with benzene (50 ml). The aqueous phase was separated and extracted with benzene (25 ml). The combined extracts were dried and filtered.

The filtrate was diluted with benzene to a volume of 410 ml and transferred to a photoreactor. It was deoxygenated by bubbling nitrogen gas through the solution for 10 minutes. Then, it was irradiated (450 Watt Hanovia medium pressure mercury lamp, pyrex sleeve) at room temperature for 0.5 hour while nitrogen gas continued to bubble through the solution. The photolyzed solution was transferred to a R-B flask, concentrated on a rotary evaporator followed by evaporation under high vacuum. The residue was then purified by flash chromatography on a silica gel column. Impurities were removed by elution was hexane:ethyl acetate (3:1/v:v to 1.5:1/v:v). Further elution was hexane:ethyl acetate (1:1/v:v) provided 6(R)-[2-[4a(S)-hydroxy-8(S)-(2,2-dimethylbutyryloxy)-2(S)-methyl-6(R)-hydroxyiminomethyl-1,2,4a,5,6,7,8,8a(S)octahydronaphthyl-1(S)]ethyl]-4(R)-(t-butyldimethylsilyloxy)-3,4,5,6-tetrahydro-2H-pyran-2-one and the titled compound 5'; NMR (CDCl₃) δ 0.075 (3H, s), 0.085 (3H, s), 0.88 (9H, s), 1.19 (3H, s), 1.20 (3H, s), 2.68 (H, s), 4.29 (H, m), 4.33 (H, d of d, J=11, 7 Hz), 4.59 (H, m), 4.97 (H, d of d, J=11, 7 Hz), 5.25 (H, m), 5.55 (H, d, J=10 Hz), 5.67 (H, d of d, J=10, 6 Hz).

(e)
6(R)-[2-[3(S)-hydroxy-8(S)-(2,2-dimethylbutyryloxy)-2(R)-methyl-6(S)-nitrosylmethyl-1,2,3,5,6,7,8,8a(S)-octahydronaphthyl-1(S)]ethyl]-4(R)-(t-butyldimethylsilyloxy)-3,4,5,6-tetrahydro-2H-pyran-2-one (6')

Cold (−20° C.) 48% aq, HF/CH₃CN (1:19/v:v, 10 ml) was added to a magnetically stirred acetonitrile solution (20 ml) of the nitrosomethyl compound 5' (750 mg, 1.29 mmol) cooled to −15° C. (ice/acetone bath). After 15 minutes the reaction was quenched by the addition of saturated NaHCO₃ solution (20 ml) and the resulting mixture was poured into ether (200 ml). The ether was washed with brine (2×25 ml) and dried over MgSO₄. Filtration and evaporation provided the title compound as a viscous pale yellow oil which was purified by flash chromatography on a silica gel column. Elution with acetone/methylene chloride (1:5.6/v:v) gave compound 6' as an oil. NMR (CDCl₃) δ 0.081 (6H, s), 0.76 (3H, d, J=7 Hz), 0.83 (3H, t, J=7 Hz), 0.89 (9H, s), 1.188 (3H,s), 1.193 (3H, s), 3.87 (2H, m), 4.30 (H, m), 4.61 (H, m), 4.79 (H, m), 5.40 (H, m), 5.74 (H, m).

(f)
6(R)-[2-[3(S)-hydroxy-6(S)-hydroxyiminomethyl-8(S)-(2,2-dimethylbutyryloxy)-2(R)-methyl-1,2,5,6,7,8,8a(S)-octahydronaphthyl-1(S)]ethyl]-4(R)-(t-butyldimethylsilyloxy)-3,4,5,6-tetrahydro-2H-pyran-2-one (7')

A magnetically stirred isopropanol solution (50 ml) containing the nitrosomethyl compound 6' (470 mg, 0.81 mmol) and pyridine (195 μl, 2.43 mmol) was heated at 95°–100° C. (oil bath) for 2 hours. The solution was cooled and concentrated in vacuo to provide the oxime 7' as a beige colored foam. NMR (CDCl₃) δ 0.079 (6H, s), 0.88 (9H, s), 2.80 and 3.40 (H, both m), 3.86 (H, m), 4.29 (H, m), 4.60 (H, m), 5.40 (H, m), 5.79 (H, m), 6.85 and 7.54 (H, both d, J=6 Hz). (g) 6(R)-[2-[6(S)-formyl-3(S)-hydroxy-8(S)-(2,2-dimethylbutyryloxy)-2(R)-methyl-1,2,3,5,6,7,8,8a(S)-octahydronaphthyl-1(S)]ethyl]4(R)-(t-butyldimethylsilyloxy)-3,4,5,6-tetrahydro-2H-pyran-2-one (8')

A 40% aqueous paraformaldehyde solution (50 ml) and acetic acid (46 μl, 0.81 mmol) were added to a solution of the oxime 7' (470 mg, 0.81 mmol) in acetone (50 ml) and the reaction mixture was stirred at ambient conditions overnight. The acetone was removed in vacuo at 25° C. and the aqueous residue was extracted with ether (2×100 ml). The ether extracts were combined, washed with brine (20 ml) and dried over MgSO₄. Filtration and evaporation in vacuo gave the crude aldehyde 8' which was purified by flash chromatography on silica gel. Elution with acetone/methylene chloride (1:9/v:v) provided the title compound as a colorless viscous oil. NMR (CDCl₃) δ 0.077 (3H, s), 0.080 (3H, s), 0.72 (3H, d, J=7 Hz), 0.81 (3H, t, J=7 Hz), 0.89 (9H, s), 1.08 (3H, s), 1.09 (3H, s), 2.91 (H, d, J=14 Hz), 3.85 (H, m), 4.29 (H, m), 4.60 (H, m), 5.39 (H, m), 5.87 (H, d, J=5 Hz), 9.64 (H, s).

(h)
6(R)-[2-[3(S)-hydroxy-6(R)-hydroxymethyl-8(S)-(2,2-dimethylbutyryloxy)-2(R)-methyl-1,2,3,5,6,7,8,8a(S)-octahydronaphthyl-1(S)]ethyl]-4(R)-(t-butyldimethylsilyloxy)-3,4,5,6-tetrahydro-2H-pyran-2-one (9')

Aluminum isopropoxide (9.76 mg, 0.048 mmol) and aluminum oxide (activated, neutral, 50 mg), were added to an isopropanol solution (10 ml) of the aldehyde 8 (54 mg, 0.0956 mmol) and the reaction mixture was stirred at 90°–95° C. (oil bath) for 58 hours. (After 22 hours more aluminum isopropoxide (19.5 mg, 0.0956 mmol) and aluminum oxide (100 mg) were added). After cooling the reaction mixture was filtered and the filtrate concentrated in vacuo to give the alcohol 9' as a viscous oil which was purified by flash chromatography on a silica gel column. Elution with acetone/methylene chloride (1:4/v:v) gave the title compound as a colorless oil. NMR (CDCl$_3$) δ 0.078 (3H, s), 0.080 (3H, s), 0.74 (3H, d, J=7 Hz), 0.83 (3H, t, J=7 Hz), 0.89 (9H, s), 1.16 (6H, s), 3.45 (2H, m), 3.84 (H, m), 4.28 (H, m), 4.61 (H, m), 5.36 (H, m), 5.72 (H, d, J=5 Hz). Further elution with the same eluant gave the 6-α-hydroxymethyl isomer as a colorless oil. NMR (CDCl$_3$) δ 0.077 (3H, s), 0.081 (3H, s), 0.76 (3H, d, J=7 Hz), 0.84 (3H, t, J=7 Hz), 0.90 (9H, s), 1.18 (3H, s), 1.19 (3H, s), 3.49 (H, dd, J=10, 6 Hz), 3.70 (H, dd, J=18 Hz, 5 Hz), 3.86 (H, m), 4.29 (H, m), 4.61 (H, m), 5.37 (H, m), 5.76 (H, d, J=5Hz).

(i)
6(R)-[2-[6(S)-hydroxymethyl-8(S)-(2,2-dimethylbutyryloxy)-2(S)-methyl-1,2,6,7,8,8a(R)-hexahydronaphthyl-1(S)]ethyl]-4(R)-hydroxy-3,4,5,6-tetrahydro-2H-pyran-2-one (I')

A solution of 48% aqueous HF/CH$_3$CN (1:19/v:v, 5 ml) was added to a magnetically stirred acetonitrile solution (5 ml) of the compound 9' (46 mg, 0.081 mmol) and the reaction mixture heated at 60° C. (oil bath) for 1 hour. The solution was cooled to 0° C. and quenched by the addition of saturated NaHCO$_3$ solution (10 ml). The resulting mixture was poured into ether (50 ml) and the ether was washed with brine (2×10 ml) and dried over MgSO$_4$. Filtration and evaporation gave the title compound I' which was purified by flash chromatography on a silica gel column. Elution of the column with acetone/methylene chloride (1:2.3/v:v) gave the title compound. NMR (CDCl$_3$) δ 0.83 (3H, t, J=7 Hz), 0.90 (3H, d, J=7 Hz), 1.13 (6H, s), 3.54 (H, m), 3.64 (H, m), 4.36 (H, m), 4.63 (H, m), 5.37 l (H, m), 5.51 (H, m), 5.79 (H, dd, J=10, 6 Hz), 6.00 (H, d, J=10 Hz).

[1] When eluted with hexane:ethyl acetate (4:1/v:v), the R$_f$ values of compound 4' and its corresponding nitrite are 0.2 and 0.32 respectively.

What is claimed is:

1. A compound of structural formula (9):

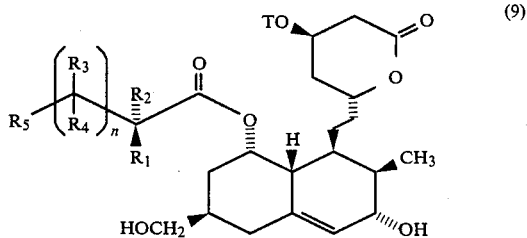

wherein:
n is 0 to 3;
R$_1$ and R$_2$ independently are hydrogen, C$_{1-5}$ alkyl, or R$_1$ and R$_2$ together with the carbon atom to which they are attached form a carbocyclic ring of 3 to 8 carbon atoms;
R$_3$ and R$_4$ are independently hydrogen, C$_{1-3}$ alkyl, C$_{3-7}$ cycloalkyl, C$_{1-3}$ alkylthio, phenyl, phenylthio or substituted phenyl in which the substituents are V and W and when n is 2 to 3, each of the R$_3$s and R$_4$s are independently hydrogen. C$_{1-3}$ alkyl, C$_{3-7}$ cycloalkyl or only one of the Rs and R$_4$s is phenyl or substituted phenyl;
R$_5$ is hydrogen, tosylate, OT, C$_{1-5}$alkyl or C$_{1-5}$alkyl substituted with tosylate or OT, or C$_{3-7}$cycloalkyl or C$_{3-7}$-cycloalkyl substituted with C$_{1-3}$alkyl, tosylate, or OT, C$_{2-5}$ alkenyl, phenyl or substituted phenyl in which the substituents are V and W, or R$_5$ is a group selected from:
(a) C$_{1-5}$-alkanoyloxy-C$_{1-4}$-alkyl,
(b)

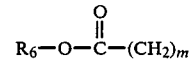

in which m is 0 to 3 and R$_6$ is C$_{1-5}$ alkyl;
(c)

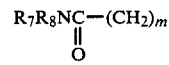

in which R$_7$ and R$_8$ are independently C$_{1-5}$ alkyl or R$_7$ and R$_8$ together with the nitrogen atom to which they are attached form a heterocycle selected from piperidinyl, morpholinyl, pyrrolidinyl, piperazinyl or thiomorpholinyl;
(d)

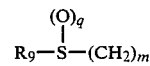

in which q is 0 to 2 and R$_9$ is C$_{1-5}$ alkyl or phenyl or substituted phenyl in which the substituents are V and W;
V and W independently are hydrogen, halogen, hydroxy, trifluoromethyl, C$_{1-3}$ alkyl, C$_{1-3}$ alkyloxy and TO-C$_{1-3}$ alkyl;
T is tert-butyldimethylsilyl, tert-butyldiphenylsilyl, trimethylsilyl, triethylsilyl, triisopropylsilyl or tetrahydropyranyl.

2. A compound of claim 1 wherein:
R$_1$ is methyl;
R$_2$ is hydrogen or methyl;
Each of the R$_3$s and R$_4$s are independently hydrogen or C$_{1-3}$ alkyl.

3. A compound of claim 2 wherein:
R$_5$ is hydrogen, tosylate, OT, C$_{1-5}$ alkyl, phenyl or substituted phenyl in which the substituents are V and W;
T is tert-butyldimethylsilyl.

4. A compound of claim 3 selected from the group wherein:
(a) n is 0, R$_2$ is methyl, R$_5$ is ethyl;
(b) n is 0, r$_2$ is hydrogen, R$_5$ is ethyl.

* * * * *